United States Patent [19]

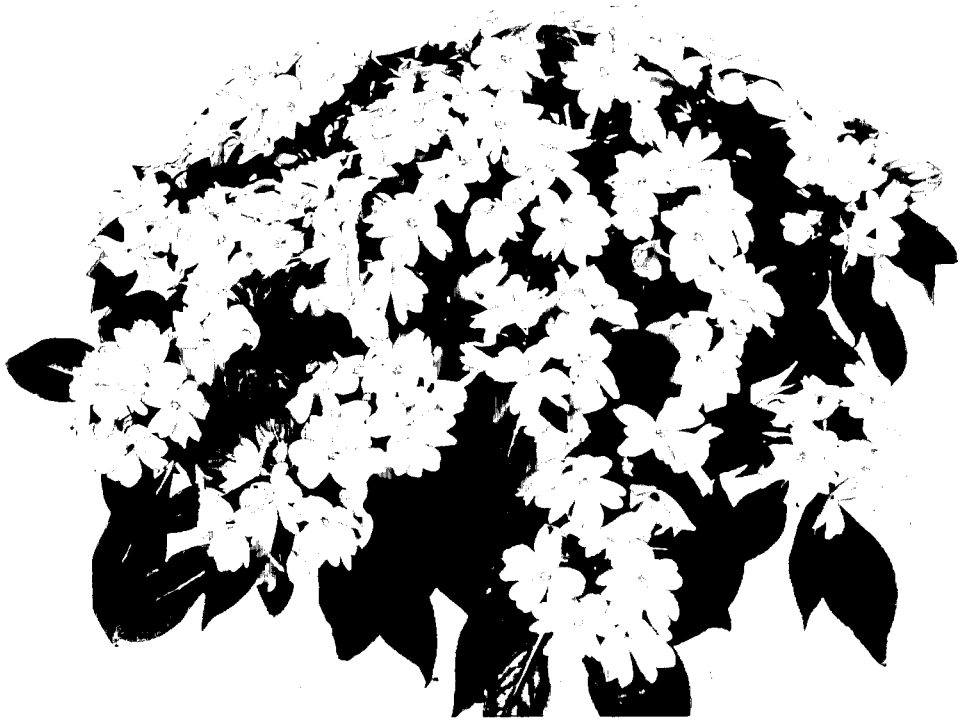

Mikkelsen

[11] Patent Number: Plant 5,780

[45] Date of Patent: Aug. 12, 1986

[54] IMPATIENS PLANT NAMED QUASAR

[75] Inventor: James C. Mikkelsen, Ashtabula, Ohio

[73] Assignee: Mikkelsens, Inc., Ashtabula, Ohio

[21] Appl. No.: 663,479

[22] Filed: Oct. 19, 1984

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

An Impatiens plant named Quasar, having multiple flowering from leaf axil, vigorous, self-branching growth habit, salmon flower color with excellent keeping quality of flowers, flowering from two (2) leaf whorls at one time making it useful for pot plant use, and by its adaptability to various environments of use.

1 Drawing Figure

The present invention relates to a new and distinctive cultivar of New Guinea Impatiens plant, botanically known as Impatiens, and referred to by the cultivar name Quasar.

Quasar was developed by me in Ashtabula, Ohio, through controlled breeding by crossing Mikkelsen Seedling No. 82-533-7 (seed parent)×Columbia (pollen parent). Columbia is enclosed in U.S. Plant Pat. No. 5,126. Asexual reproduction by terminal or stem cuttings taken by me in Ashtabula, Ohio, has shown that the unique features of this new Impatiens are stabilized and are reproduced true to type in successive propagations.

The following characteristics distinguish Quasar from both its parent varieties and other cultivated Impatiens of this type known and used in the floriculture industry:

1. Larger, more vigorous plant than Solared (U.S. Plant Pat. No. 5,131). Plant size is similar to Columbia, Comet and Pulsar but not as large as Twilight. Comet, Pulsar and Twilight are cultivars of the present inventor disclosed in pending applications.

2. Flower color is a salmon orange that is deeper in color than Meteor (unpatented) and Sunfire (unpatented) and similar to Sunset (unpatented). Flowers are deeper in color during the winter months.

3. Flowers have excellent keeping qualities and range from below the foliage to over the top of the foliage. This cultivar flowers from 2 or more whorls of leaves at one time as 2 flowers develop at leaf axil instead of only one.

4. New cultivar is self-branching, and a vigorous grower having a semi-mounted growth form, thereby making it ideal for pot, hanging basket and bedding plant use.

5. Leaf color is less intense than Solared, and leaf size is similar to Columbia. There is some basal variegation at the midrib, and the central vein is reddish pink at the base.

6. Plant and flowers have good low temperature tolerance as demonstrated by being able to withstand two (2) nights of 2.2° C. temperature in early May while continuing to grow and flower.

7. Flowering begins earlier than Solared and Columbia as Quasar sets buds very quickly; similar in earliness to Comet and Pulsar.

8. The early flowering and multiple flowers at a leaf axil makes this variety excellent for hybridization work for pot plant development with floriferous habit.

9. After several months of growth and flowering, the flowers nearly cover the foliage, as illustrated.

The accompanying colored photograph taken in March 1984 illustrates the overall appearance in perspective view of Quasar, and showing the colors as true as it is reasonably possible to obtain in a colored reproduction of this type. The color photograph depicts winter flower color.

The following is a detailed description of my new Impatiens cultivar based on plants produced under commercial practices in Ashtabula, Ohio, grown in 5.5" green plastic pots during the winter of 1983–1984, and describes floriferous flowering and deeper coloring of Quasar under low light environment. Color references are made to The Royal Horticultural Society Colour Chart except where general terms of ordinary dictionary significance are used.

Parentage: Mikkelsen Seedling No. 82-533-7×Columbia.

Propagation:

(A) *Type cutting.*—Stem 15 mm long will develop 4.5 long in 18 to 21 days.

(B) *Time to root.*—8 to 10 days at 23° C. summer, 10 to 12 days at 20° C. winter.

(C) *Rooting habit.*—Large mass of fiberous roots from the stem.

Plant description:

(A) *Form.*—Symmetrical, semi-mounded, compact, self-branching, flowering herb, with pale red stems.

(B) *Habit of growth.*—Vigorous, self-branching, compact, with continuous flowering.

(C) *Foliage description.*—Light green leaves with a trace of variegation and a reddish main vein at the basal end. (1) Size: 6.0 to 6.5 cm long×3.5 to 3.75 cm. (2) Shape: Lanceolate to ovate with acuminate apex on acute base. (3) Texture: Rugose upper side, glabrous under side. (4) Margin: Serrated, finely ciliated. (5) Color: Young foliage, top side 137A, under side 138B. Mature foliage, top side 147A, under side 174C. (6) Venation: Pinnate.

Flowering description:

(A) *Flowering habits.*—Flowers continuously from leaf whorl in progressive, orderly manner. However, instead of 1 flower per leaf axil this cultivar has 2 flowers per axil thus doubling the numbers of flowers per plant. It takes 5 to 7 days from bud showing color to bloom; flowers last 2 to 3 weeks.

(B) *Natural flowering season.*—Indeterminant and continuous. Quantity of flowers increase with increasing levels of light intensity and duration.

(C) *Flower buds.*—Ellipsoidal, flowers perfect, reddish spur 3.75 cm long on mature bud with throat behind ovary and originating from the major sepal.

(D) *Flowers borne.*—On individual short pedicels from whorl of 5 leaves, flowering progressively around the whorl as leaves and bud develop (2 flower buds/leaf with second opening after all five first flowers have opened); flowers both above and in the leaf canopy.

(E) *Quantity of flowers.*—Extremely floriferous; flowering is continuous so that tight buds to mature blooms are visible at the same time in large numbers.

(F) *Petals.*—(1) Shape: Heart shaped, top dominant, all five petals overlap. (2) Color: Top side in summer when opening 41C, maturing to 40D; top side in winter when opening 50C, fading to 48C-D (Note: color deepens rather than fades.); under side in summer 41D to 43D, in winter 48C. (3) Number of petals: Five (5) in number. (4) Size of flowers: 5.0 to 6.0 cm.

(G) *Reproductive organs.*—(1) Stamens: Five (5) in number. (a) Anther shape: Hooded, 47C. (b) Pollen color: Cream. (2) Pistils (a) Stigma shape: Five (5) in number, segmented column, white in color. (b) Style color: Clear. (c) Ovaries: Five (5) in number, celled 4 mm until fertilized, green in color.

Disease resistance: No significant disease or insect problems have been seen to date.

I claim:

1. A new and distinct cultivar of New Guinea Impatiens plant named Quasar, as described and illustrated, and particularly characterized by its multiple flowering from leaf axil, vigorous, self-branching growth habit, salmon flower color with excellent keeping quality of flowers, flowering from two (2) leaf whorls at one time making it useful for pot plant use, and by its adaptability to various environments of use.

* * * * *